United States Patent
Son et al.

(10) Patent No.: US 6,699,287 B2
(45) Date of Patent: Mar. 2, 2004

(54) DERMAL SCAFFOLD USING ALKALINE PRE-TREATED CHITOSAN MATRIX OR ALKALINE PRE-TREATED CHITOSAN AND ALKALINE PRE-TREATED COLLAGEN MIXED MATRIX

(75) Inventors: Young-Sook Son, Seoul (KR); Yong-Ha Youn, Incheon (KR); Seok-Il Hong, Seoul (KR); Seung-Hoon Lee, Seoul (KR); Yong-Jae Gin, Seoul (KR); Kyu-Bo Han, Sungnam-si (KR); Chun-Ho Kim, Seoul (KR)

(73) Assignee: Korea Atomic Energy Research Institute, Daejeon (KR)

( * ) Notice: Subject to any disclaimer, the term of this patent is extended or adjusted under 35 U.S.C. 154(b) by 14 days.

(21) Appl. No.: 10/132,869

(22) Filed: Apr. 25, 2002

(65) Prior Publication Data

US 2002/0161440 A1 Oct. 31, 2002

Related U.S. Application Data

(63) Continuation-in-part of application No. 09/399,547, filed on Sep. 20, 1999, now abandoned.

(51) Int. Cl.$^7$ .................................................. A61F 2/16
(52) U.S. Cl. ................................ 623/15.12; 623/15.11
(58) Field of Search ........................ 623/14.13, 15.11, 623/15.12, 23.72, 23.76

(56) References Cited

U.S. PATENT DOCUMENTS

| | | | |
|---|---|---|---|
| 5,207,582 A | | 5/1993 | Michelson |
| 5,420,197 A | * | 5/1995 | Lorenz et al. ............. 525/54.3 |
| 5,460,939 A | * | 10/1995 | Hansbrough et al. ........ 435/1.1 |
| 5,474,064 A | | 12/1995 | Rohrberg |
| 5,494,442 A | | 2/1996 | Hecht |
| D377,832 S | | 2/1997 | Jacober |
| 5,657,753 A | | 8/1997 | Jacober |
| 5,863,984 A | | 1/1999 | Doillon et al. ............. 525/54.1 |
| 6,454,811 B1 | * | 9/2002 | Sherwood et al. ........ 623/23.76 |

OTHER PUBLICATIONS http://www.genis.is/chitininni.htm.*
Berschet, et al.; Biomedicals, vol. 15, No. 8, 593–600 (1994).
Hansborough, MD, et al., Journal of Burn Care & Rehabilitation, vol. 14, No. 5, 85–494 (1993).
Hansborough, MD, et al., Surgery, vol. 111, 438–446 (1992).
Woerly, et al., Biomedicals, vol. 17, No. 3, 301–310 (1996).
Marcinkowska, et al., Biomedical and Biophysical Research Communications, 241, 419–426 (1997).
Weadock, et al., Journal of Biomedical Materials Research, vol. 29, 1373–1379 (1995).
Kuroyanagi, et al., Annals. of Plastic Surgery, vol. 31, No. 4, 340–349 (1993).
Berthod, et al., The Journal of Investigative Dermatology, vol. 108, No. 5, 737–742 (1997).

* cited by examiner

*Primary Examiner*—Corrine McDermott
*Assistant Examiner*—Hieu Phan
(74) *Attorney, Agent, or Firm*—Edwards & Angell, LLP; Dianne M. Rose; Peter Corless

(57) ABSTRACT

Disclosed are a dermal scaffold comprising alkaline pre-treated free amine-containing chitosan matrix, alkaline pre-treated free amine-containing chitosan and alkaline pre-treated collagen mixed matrix, or alkaline pre-treated free amine-containing chitosan and alkaline pre-treated collagen mixed matrix containing chitosan fabrics, which has excellent wound healing effect by constituting microenvironments suitable for migration and proliferation of fibroblasts and vascular cells surrounding the wound to be extremely useful as wound healing dressings, and a bioartificial dermis comprising the dermal scaffold and human fibroblasts, particularly useful for healing broad wound sites such as burns.

8 Claims, 17 Drawing Sheets

(17 of 17 Drawing Sheet(s) Filed in Color)

Fig.2
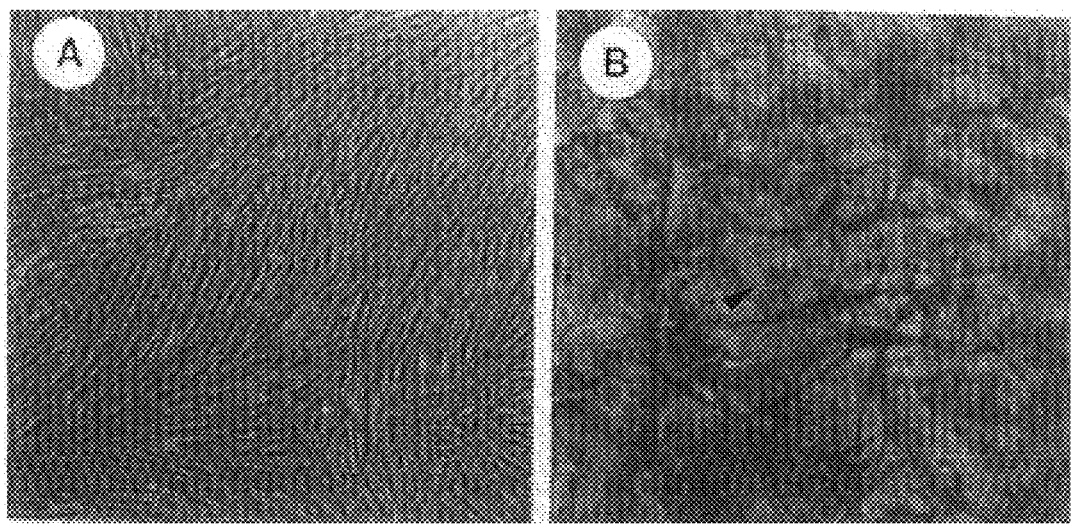
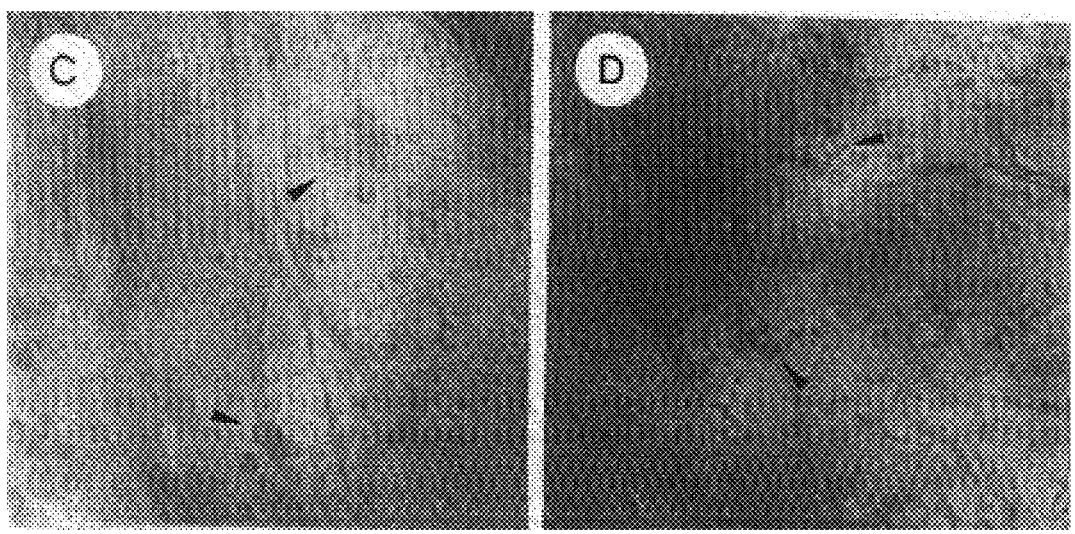

Fig. 11 (continue)
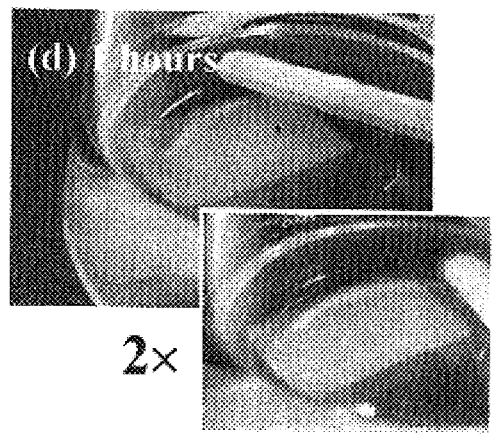
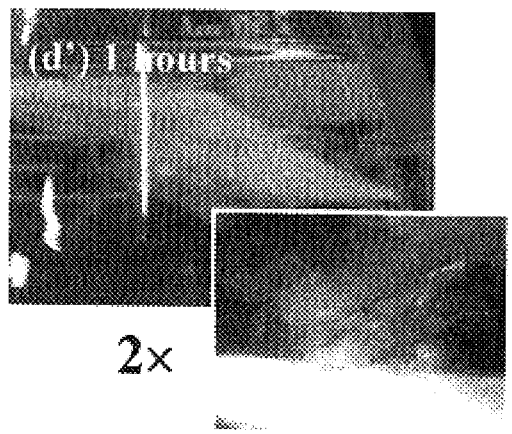
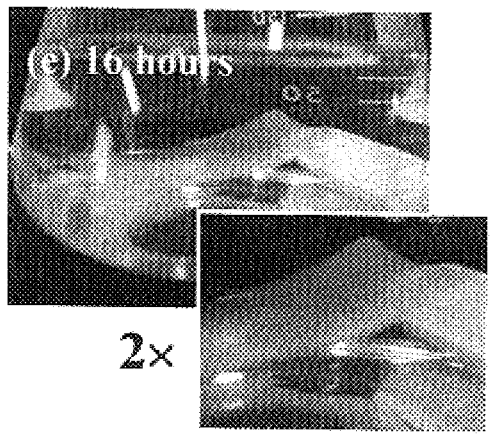
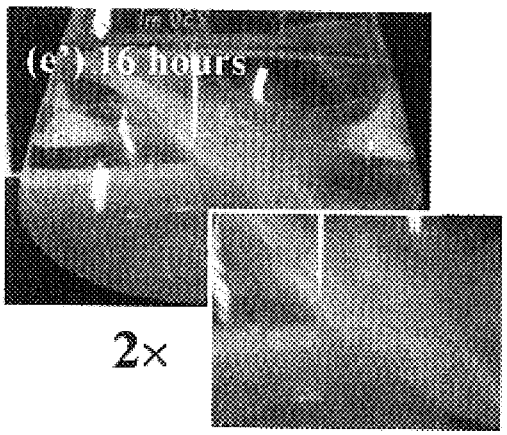

Fig. 12
Sponge type
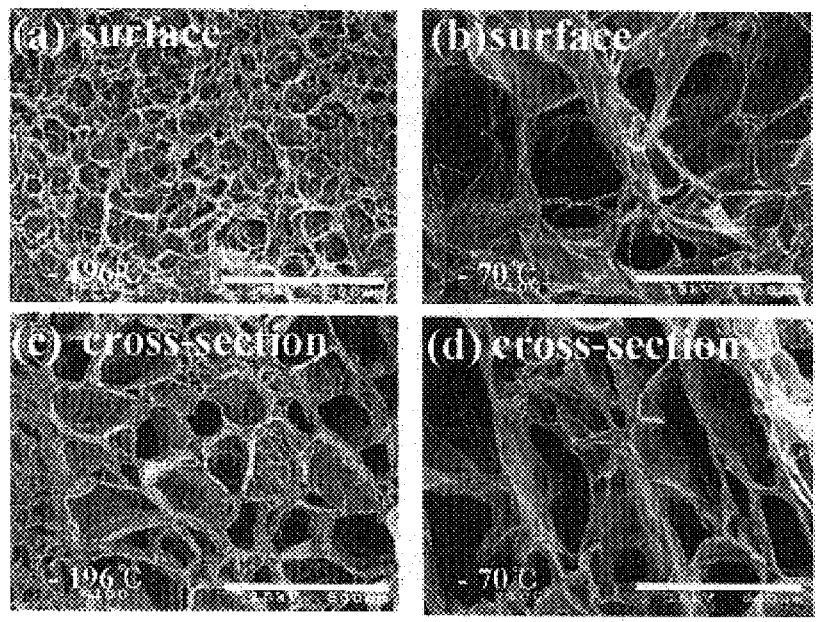
Mesh type
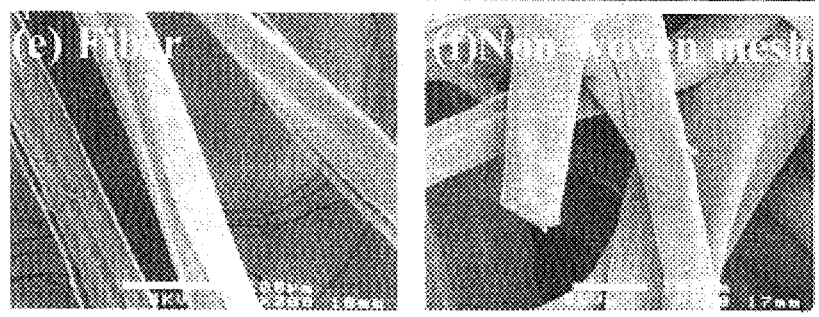
Cell-loaded Sponge
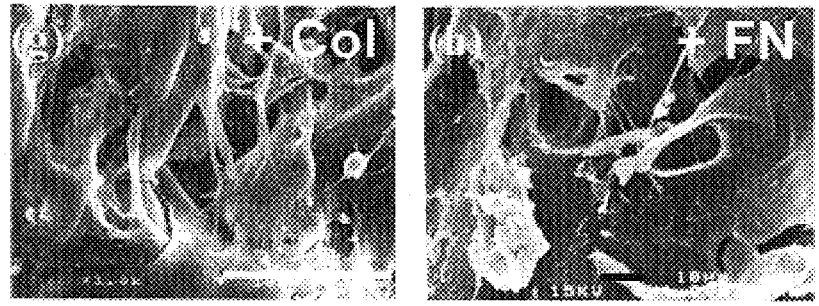

Fig. 14  7 days  15 days 7 days     15 days

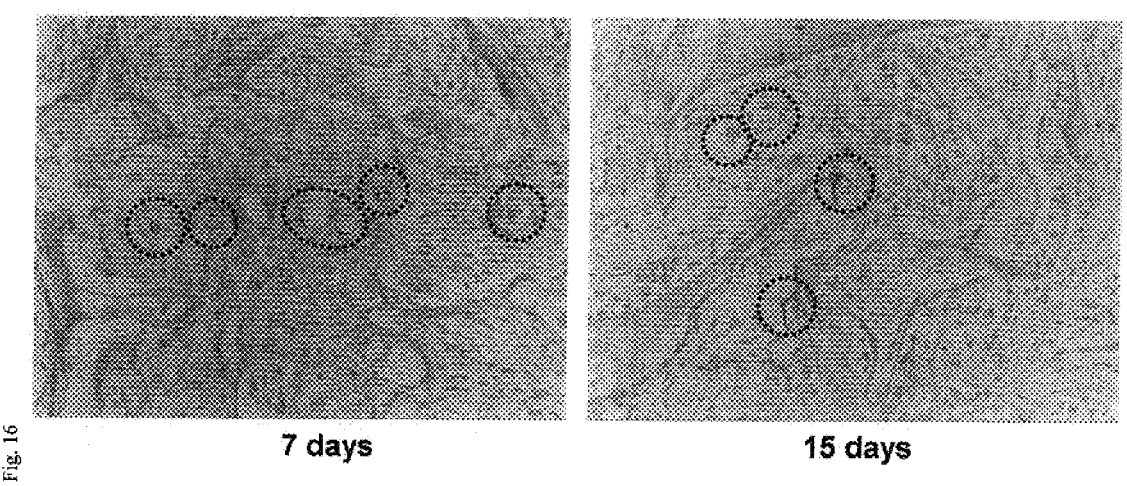
Fig. 16    7 days    15 days

DERMAL SCAFFOLD USING ALKALINE PRE-TREATED CHITOSAN MATRIX OR ALKALINE PRE-TREATED CHITOSAN AND ALKALINE PRE-TREATED COLLAGEN MIXED MATRIX

RELATED APPLICATIONS

This application is a continuation-in-part and claims priority under 35 U.S.C. §120 to U.S. patent application Ser. No. 09/399,547, now abandoned, filed Sep. 20, 1999, which claims priority under 35 U.S.C. §119 to 1998-39576 (Republic of Korea), filed Sep. 24, 1998, the entireties of which are incorporated by reference herein.

FIELD OF THE INVENTION

The present invention relates to a dermal scaffold and a bioartificial dermis using the same. More specifically, the present invention relates to the dermal scaffold and the bioartificial dermis comprising alkaline pre-treated free amine-containing chitosan matrix, alkaline pre-treated free amine-containing chitosan and alkaline pre-treated collagen mixed matrix, or alkaline pre-treated free amine-containing chitosan and alkaline pre-treated collagen mixed matrix containing chitosan fabrics, which are extremely useful for wound healing therapy.

BACKGROUND

Various kinds of ordinary dressings for wound healing have been hitherto developed and conveniently used, but in most cases, they have been used only for the prevention of infection or dehydration.

Recently, acellular artificial skins or cell-based bioartificial skins have been developed and marketed by many biotechnological companies. As examples, acellular artificial skins, such as an acellular collagen-glycosaminoglycan matrix bonded to a thin silicone membrane (INTEGRA™, Interga LifeSciences Co.) and dehydrorothermally cross-linked composites of fibrillar and denatured collagens (Terudermis™, Terumo Co.), are now commercially available. However, such products are very expensive because they incorporate biomaterials such as collagen and thus, have difficulty in clinical trials on broad wound sites, e.g., burns.

As cell-based bioartificial skins, Advanced Tissue Sciences, Inc. (La Jolla, Calif.) developed a skin replacement product composed of a thin biodegradable mesh framework onto which human dermal fibroblasts (hereinafter, abbreviated as "HDF" on occasion) are seeded, for use in treating diabetic foot ulcers (Dermagraft-TC™). In addition, epidermal cell sheet for partial-thickness wound (Acticel™, Biosurface Technology, Inc.), composite grafts of cultured keratinocytes and fibroblasts on a collagen glycosaminoglycan matrix (Apligraft™, Organogenesis, Inc.) and a skin replacement product derived from human cadaver skin (Alloderm™, Lifecell), etc., were developed.

The cell-based bioartificial skins were prepared by primary culture of human dermal fibroblasts and keratinocytes followed by 3-dimensional culture (3-D culture, raft culture) of the cultured cells in hydrated collagen. They had considerably good wound healing and scar reducing effects in clinical trials on burn or plastic surgery patients. However, they still have problems in that they are too expensive due to incorporation of collagen (e.g. Dermagraft-TC: $2,000/ 10×10 cm, Terudermis: $1,500) and are limited in their uses as grafts due to a low rigidity of hydrated collagen gel.

Therefore, there still exists an important demand for development of polymers with good biocompatibility and biodegradability, which can successfully replace collagen and is also suitable for use as a scaffold.

To be a dermal scaffold, porous microstructures are required either to allow tissue ingrowth in vivo or to provide a template for directed tissue assembly in vitro. The skin equivalent is ideally reconstructed by grafting human epidermal keratinocytes onto a porous non-contractile dermal equivalent populated with mitotically and metabolically active HDFs. Among natural polymers that can be easily formed into a porous spongy matrix, there is a particular interest in chitosan. Chitosan is a linear polysaccharide obtained from partial deacetylation of chitin that can be derived from arthropod exoskeletons. Chitin is slowly degraded in vivo and thus, chitin and its degradation products are natural and safe. In the pharmaceutical field, chitosan has been used as a vehicle for the sustained release of drugs (Hou et al., Chem Pharm Bull 1985; 33(9):3986–3992). Chitin as such has been woven into fabrics and used as dressings for wound healing.

Particularly, Lorenz et al. (U.S. Pat. No. 5,420,197) described a hydrophilic hydrogel which comprised a blend of acid neutralized water-soluble chitosan and poly(N-vinyl lactam). In the patent, neutralized water-soluble chitosan means chitosan protonated with acids, which becomes soluble in water, e.g. salts with pyrrolidone carboxylic acid, glutamic acid, acetic acid, etc. and N,O-carboxymethyl chitosan (NOCC). The resulting gel may be used as a wound dressing because of its non-adherence property to the wound.

Berscht et al. (Biomaterials 1994; 15(8); 593–600) disclosed methylpyrrolidinone chitosan (MPC), one of the water-soluble chitosan derivatives, as a carrier material for growth factors. However, water-soluble chitosan derivatives are easily dissolved in water, PBS, saline or culture media. They cannot maintain the original shapes and the structural integrity for the ingrowth of stromal fibroblasts and the formation of microvessel, which is an essential feature of a dermal scaffold.

Hansbrough et al. (U.S. Pat. No. 5,460,939) described a temporary living skin replacement comprising: a) a living stromal tissue enveloping b) a three-dimensional structural framework composed of a biodegradable or non-biodegradable material, and c) a transitional covering made of silicone or polyurethane. According to the patent, the framework may be composed of chitosan or its derivatives. However, it is a mesh type, which is more brittle and stiff, and less tensile than a spongy type. Further, NOCC, one example of a chitosan derivative described, is soluble in water. NOCC can be spun into fiber using coagulation baths containing $Ca^{2+}$ or other similar di- or trivalent cations. However, the detached cations from degraded dressing could cause significant damages to stromal cells.

Therefore, it has never been reported that chitosan matrix having free amine group by alkaline pre-treatment of an acidic chitosan solution, which is insoluble in water, can be used as a dermal scaffold, providing a structural integrity for migration and proliferation of fibroblasts and vascular endothelial cells surrounding wound site.

SUMMARY OF THE INVENTION

Accordingly, in order to solve the above-mentioned problems involved in the prior art, an object of the present invention is to provide a novel dermal scaffold for wound healing with excellent biocompatibility and biodegradability, which is not only cost-effective but also convenient to manipulate owing to its improved rigidity. In one aspect of the invention, the dermal scaffold further comprises one or more growth factors, e.g., such as basic fibroblast growth factor (bFGF), fibronectin, etc., for accelerating wound healing.

Another object of the present invention is to provide a bioartificial dermis wherein human fibroblasts are loaded onto the dermal scaffold, particularly useful for healing of broad wound sites such as burns.

In order to attain the above-described objects, one aspect of the present invention provides a dermal scaffold comprising alkaline pre-treated chitosan matrix, alkaline pre-treated chitosan and alkaline pre-treated collagen mixed matrix, or alkaline pre-treated chitosan and alkaline pre-treated collagen mixed matrix containing chitosan fabrics. The dermal scaffold preferably further comprises one or more selected from the group consisting of fibronectin, basic fibroblast growth factor, epidermal growth factor and transforming growth factor-β.

Another aspect of the present invention provides a bioartificial dermis wherein human fibroblasts are loaded onto alkaline pre-treated chitosan matrix, alkaline pre-treated chitosan and alkaline pre-treated collagen mixed matrix, or alkaline pre-treated chitosan and alkaline pre-treated collagen mixed matrix containing chitosan fabrics.

In the present invention, chitosan is pre-treated with an alkaline solution thereby to become insoluble in water. The matrices of the present invention are characterized in that they are made of such the alkaline pre-treated chitosan that is insoluble in an aqueous medium or a body fluid. Therefore, it can provide a structural integrity for migration and proliferation of wound healing cells, such as fibroblasts and vascular endothelial cells, surrounding wound site.

BRIEF DESCRIPTION OF THE DRAWINGS

"The file of this patent contains at least one drawing or photograph executed in color. Copies of this patent with color drawing(s) or photograph(s) will be provided by the Patent and Trademark Office upon request and payment of necessary fee."

The objects and features of the invention can be better understood with reference to the following detailed description and accompanying drawings.

FIG. 2 shows chitosan matrix with cultured human fibroblasts viewed using light microscopy (magnification×200);

FIG. 12 shows SEM morphologies of the sponge types of chitosan fibers prepared at different processing temperatures, the mesh type of non-woven chitosan scaffolds, and cell-loaded chitosan scaffolds;

DETAILED DESCRIPTION

Figure 1:
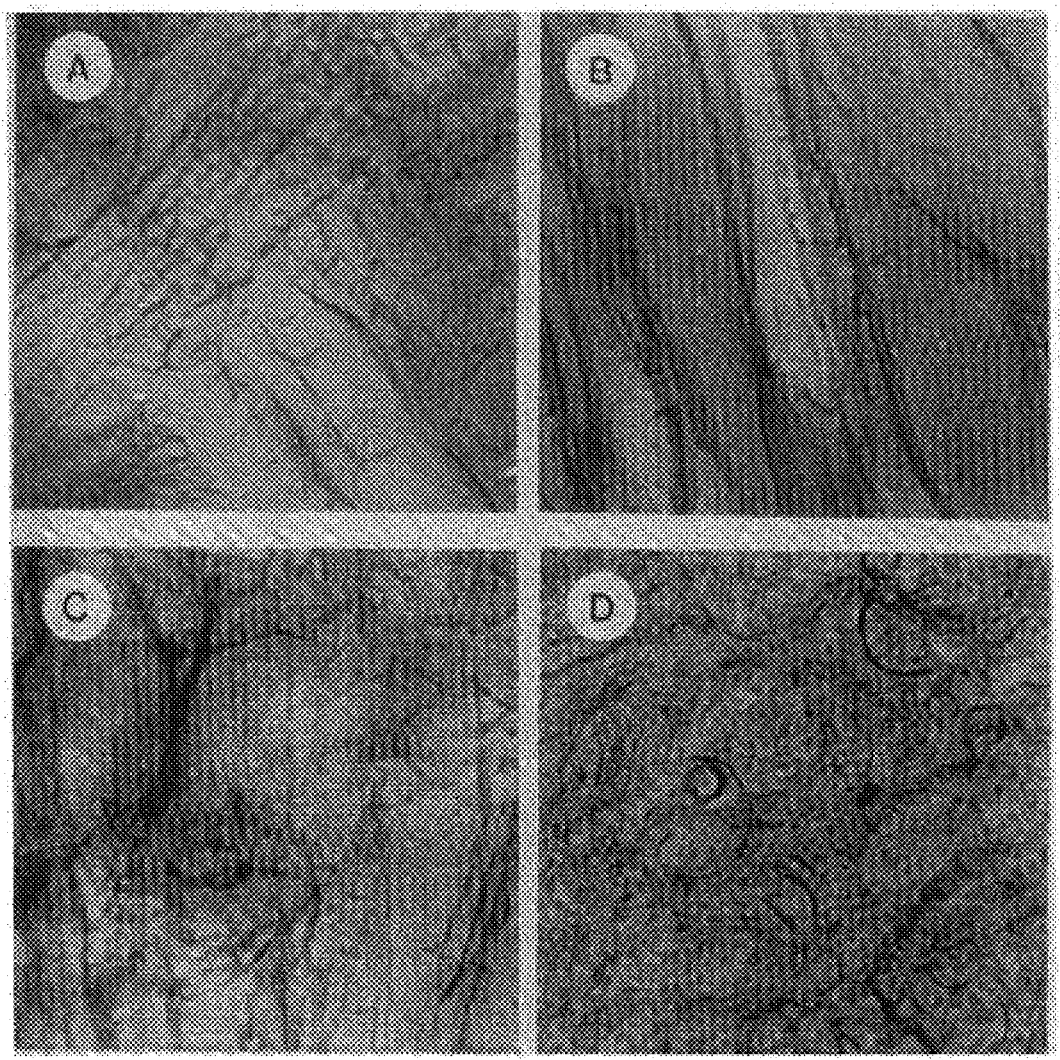
FIG. 1 shows prepared chitosan and collagen matrices viewed using light microscopy of (magnification×200)

The present inventors unexpectedly found that spongy matrix scaffold could be obtained by pre-treatment of an acidic chitosan solution with an alkaline solution followed by lyophilization of the alkaline pre-treated chitosan solution. The obtained alkaline pre-treated free amine-containing chitosan spongy matrix is cost-effective compared to the art-known collagen matrix products and has the improved rigidity which allows it to be conveniently manipulated. Further, it can be grafted onto the wounded tissue thereby to exhibit excellent wound healing effect, and therefore, would be extremely useful as dressings for wound healing.

In order to prepare the dermal scaffold comprising alkaline pre-treated free amine-containing chitosan matrix according to the present invention, first, an acidic chitosan solution is mixed with an alkaline solution to obtain an alkaline pre-treated chitosan solution. According to the present invention, the acidic chitosan solution is preferably prepared by dissolving chitosan in 1% acetic acid solution at concentrations of 1 to 2 w/v %. As the alkaline solution for pre-treatment, a mixed solution of reconstruction buffer (2.2 g of $NaHCO_3$, 4.77 g of HEPES (200 mM)/100 ml of 0.05 N NaOH) and 10× medium free of $NaHCO_3$ (DMEM:F12= 3:1, Gibco BRL. DMEM-Cat. No. 12800-058, F12-Cat. No. 21700-026) is preferably used. The alkaline pre-treated chitosan solution is frozen at a low temperature, particularly, at −70° C. for one day or under liquid nitrogen (at about −140° C.) and then, lyophilized (−42° C.) to obtain a spongy matrix dermal scaffold. The obtained dermal scaffold is sterilized and then applied to wound sites. In the present invention, γ-ray or ultraviolet irradiation, or 70% ethanol soaking is preferably employed for sterilization. Especially, γ-ray (5–30 kGy/5 hrs, γ-ray source; $Co^{60}$) and ultraviolet irradiation can induce cross-linkage of chitosan and collagen, respectively.

In order to increase biocompatibility of the alkaline pre-treated free amine-containing chitosan matrix according to the present invention, alkaline pre-treated chitosan and alkaline pre-treated collagen mixed matrix may be employed. The alkaline pre-treated chitosan and alkaline pre-treated collagen mixed matrix may be prepared by mixing the alkaline pre-treated chitosan solution prepared as above with an alkaline pre-treated type-Ip collagen (atelomeric collagen) solution prepared according to the substantially same procedure as the alkaline pre-treated chitosan solution. Preferably, a mixing ratio is preferably adjusted for a weight ratio of collagen to chitosan to be in the range of 1:8 to 1:2 based on a final product. However, it may be appropriately varied considering the desired rigidity and histological characteristics of the wounded tissue. Since collagen is likely to form a gel at room temperature, preparation and alkaline pre-treatment of the collagen solution is preferably performed at 4° C. or less.

In order to increase tensility of the alkaline pre-treated chitosan matrix, alkaline pre-treated chitosan and alkaline pre-treated collagen mixed matrix containing chitosan fabrics may be prepared. More specifically, chitosan fibers may be woven into fabrics according to any conventional method. Onto the woven chitosan fabrics is placed the alkaline pre-treated chitosan solution, and alkaline pre-treated chitosan matrix containing chitosan fabrics is prepared according to the above-described procedure. Then, to increase attachment of human fibroblasts, the prepared matrix is coated with the alkaline pre-treated type-Ip collagen solution to obtain alkaline pre-treated chitosan and alkaline pre-treated collagen mixed matrix containing chitosan fabrics.

Alkaline pre-treated chitosan matrix, alkaline pre-treated chitosan and alkaline pre-treated collagen mixed matrix or alkaline pre-treated chitosan and alkaline pre-treated collagen mixed matrix containing chitosan fabrics may further comprise fibronectin, basic fibroblast growth factor, epidermal growth factor, transforming growth factor-β, etc. In the present invention, the spongy matrix preferably comprises 50 to 500 ng/ml of fibronectin or 10 to 100 ng/ml of basic fibroblast growth factor.

In addition, a bioartificial dermis prepared by loading human fibroblasts onto the matrix is useful for wound healing by being grafted onto the relatively broad wound sites. The bioartificial dermis may be prepared by loading $1–5\times10^5$ cells/$cm^2$ onto the matrix followed by culturing it under conditions suitable for attachment and proliferation of human fibroblasts. However, for emergency, it will be allowed to graft the bioartificial dermis comprising human fibroblasts cultured for just one day.

In the present alkaline pre-treated chitosan, or alkaline pre-treated chitosan and alkaline pre-treated collagen mixed matrix, any shapes such as round, square, etc., may be allowed. Further, size and thickness thereof may be appropriately varied in accordance with application sites and particularly, it may be molded into various shapes, e.g. nose, ear, etc.

EXAMPLES

This invention will be better understood from the following examples. However, one skilled in the art will readily appreciate the specific materials and results described are merely illustrative of, and are not intended to, nor should be intended to, limit the invention as described more fully in the claims which follow thereafter.

Examples 1

Preparation of a Dermal Scaffold (1) Preparation Of A Dermal Scaffold Comprising Chitosan Matrix Weighed amounts of chitosan (Fluka, medium MW; ~400,000) were dissolved in 1 v/v % acetic acid to give 2 w/v % solutions. The solutions were stirred for 1 hour at room temperature and then, incubated overnight at room temperature to remove entrapped air bubbles from the solutions in a dust-free atmosphere. 20 ml of the solutions were added to plastic petri-dishes having a diameter of 100 mm (to prepare round matrix having a diameter of 100 mm) and allowed to stand overnight at −70° C. The frozen solutions were lyophilized in a freeze-dryer for 48 hours to obtain a chitosan matrix. The matrix was washed with phosphate buffered saline three times. Subsequently, the obtained chitosan matrix was frozen and lyophilized again under the same condition as above and then, irradiated by γ-ray (20 kGy/5 hrs, γ-ray source; $Co^{60}$). 30 W Ultraviolet was irradiated on each surface of this matrix at a distance of 30 cm for 1 hour to make the matrix insoluble in water. Thus, a spongy matrix dermal scaffold having a thickness of 3.0–4.0 mm was obtained.

The obtained chitosan matrix was smooth and flexible and composed of chitosan fibers to be porous. FIG. 1 shows the semi-transparent chitosan matrix under a phase-contrast light microscopy (A).

(2) Preparation Of A Dermal Scaffold Comprising Alkaline Pre-Treated Free Amine-Containing Chitosan Matrix In order to prepare an alkaline pre-treated chitosan matrix, 2 w/v % chitosan solution dissolved in acetic acid, reconstruction buffer (2.2 g of $NaHCO_3$, 4.77 g of HEPES (200 mM)/ 100 ml of 0.05 N NaOH) and 10× medium free of $NaHCO_3$ (DMEM:F12=3:1, Gibco BRL. DMEM-Cat. No. 12800-058, F12-Cat. No. 21700-026) were mixed in a ratio of 8:1:1 to obtain an alkaline pre-treated chitosan solution. Alkaline pre-treated chitosan matrix was prepared using the alkaline pre-treated chitosan solution according to the same procedure as Example 1(1). FIG. 1 shows the semi-transparent alkaline pre-treated free amine-containing chitosan matrix under a phase-contrast light microscopy (B).

(3) Preparation Of A Dermal Scaffold Comprising Alkaline Pre-Treated Free Amine-Containing Chitosan And Alkaline Pre-Treated Collagen Mixed Matrix In order to prepare an alkaline pre-treated collagen solution, type-Ip collagen (3 mg/ml at a pH of 3.0; Cell matrices, Gelatin Corp., Osaka, Japan, swine collagen free of telomeric portion by treatment with pepsin) solution, reconstruction buffer and 10× medium free of $NaHCO_3$ were mixed in a ratio of 8:1:1. Then, the mixed solution was alkaline pre-treated. Alkaline pre-treatment and manipulation of the collagen solution were performed at 4° C. or less. The obtained alkaline pre-treated collagen solution and the alkaline pre-treated chitosan solution prepared in Example 1(2) were mixed in a ratio of 1:1 (v/v) to obtain a solution for preparation of a chitosan and collagen mixed matrix (as a final concentration, 8 mg/ml of chitosan, 1.2 mg/ml of collagen). A dermal scaffold was prepared using the chitosan and collagen mixed solution according to the substantially same procedure as Examples 1(1) and (2). FIG. 1 shows the semi-transparent alkaline pre-treated chitosan and alkaline pre-treated collagen matrix (C) and type-Ip collagen matrix (D) under a phase-contrast light microscopy.

(4) Preparation Of An Alkaline Pre-Treated Free Amine-Containing Chitosan And Alkaline Pre-Treated Collagen Mixed Matrix Containing Chitosan Fabrics In order to increase tensility of the alkaline pre-treated chitosan matrix, alkaline pre-treated chitosan and alkaline pre-treated collagen mixed matrix containing chitosan fabrics was prepared as follows.

First, chitosan fibers were woven into fabrics according to any conventional method. Onto the woven chitosan fabrics was placed the alkaline pre-treated chitosan solution prepared in Example 1(2) and alkaline pre-treated chitosan matrix containing chitosan fabrics was prepared according to the substantially same procedure as Example 1(1). Then, to increase attachment of human fibroblasts, the prepared matrix was coated with the alkaline pre-treated type-Ip collagen solution prepared in Example 1(3) to obtain chitosan and collagen mixed matrix containing chitosan fabrics.

The alkaline pre-treated chitosan and alkaline pre-treated collagen mixed matrix containing chitosan fabrics according to the present example has the improved tensility and may be conveniently manipulated and stored.

(5) Preparation Of A Dermal Scaffold Comprising Fibronectin And Basic Fibroblast Growth Factor To the solutions for preparing chitosan, alkaline pre-treated free amine-containing chitosan, and alkaline pre-treated free amine-containing chitosan and alkaline pre-treated collagen mixed matrix prepared in Examples 1(1) to (3) was added fibronectin or basic fibroblast growth factor at concentrations of 5, 50 and 500 ng/ml, respectively. In the above case, a final matrix comprised 0.67 ng/8 mm-diameter matrix of fibronectin and 0.33 ng/8 mm-diameter matrix of basic fibroblast growth factor, respectively.

A dermal scaffold was prepared using the mixed solution according to the substantially same procedure as Examples 1(1) to (3) except performing γ-ray irradiation (5 kGy/5 hrs, γ-ray source; $Co^{60}$).

Example 2

Preparation of a Bioartificial Dermis (1) Primary Pure Culture Of Human Dermal Fibroblasts HDFs were isolated from neonatal foreskin obtained aseptically after circumcision. Dermis was separated from epidermis by incubation in 0.25% trypsin/0.02% EDTA solution for one hour at 37° C. Dermis was minced and digested with 0.35% collagenase B solution for one hour at 37° C. The obtained cells were washed several times to remove collagenase and then, the cells were suspended in DMEM medium supplemented with 10% fetal bovine serum. Fibroblasts were cultured in a tissue culture flask at 37° C., 5% $CO_2$, in a humidified incubator. After reaching a confluency of 80~90%, the cells were subcultured using 0.1% trypsin solution. The standard number of the suspended cells in the subculture was $1 \times 10^6$ cells/100 mm dish. The cells were stored in a cryopreserved solution (DMEM 50%, fetal bovine serum 40%, DMSO 10%). Before preparation for loading onto a dermal scaffold, the cells were thawed and recultured. To prepare a bioartificial dermis, the cryopreserved cells were diluted with phosphate buffered saline and centrifuged three times. Then, the cells were washed, suspended in the medium and recultured. FIG. 2 shows the primary pure cultured human dermal fibroblasts (A).

(2) Attachment Of Human Dermal Fibroblasts Into A Dermal Scaffold

In a laminar-flow hood, the matrices were punched at diameters of 8 mm and 100 mm and placed in a culture dish (24 wells, a diameter of 150 mm). To prepare round matrix having a diameter of 8 mm, $1 \times 10^5$ viable cells (determined by trypan blue solution) were diluted with minimum volume of DMEM medium and placed onto the matrix. Then, it was allowed to stand at 37° C., 5% $CO_2$ for 4 hours and 50 μl of DMEM medium was further added thereto. 24 hours after the addition, 1 ml of the medium was added to each well and the cells were cultured. The artificial dermis was maintained under the same condition as above for 4 weeks to reach a constant confluency. All the cells and tissue matrices formed adhering to the matrices were observed under a phase-contrast light microscopy. The medium was replaced three times a week.

FIG. 2 shows alkaline pre-treated chitosan matrix comprising human fibroblasts (B), alkaline pre-treated chitosan matrix comprising fibronectin (C) and alkaline pre-treated chitosan and alkaline pre-treated type-Ip collagen mixed matrix comprising fibronectin (D), respectively.

(3) Evaluation Of Human Dermal Fibroblasts Viability And Growth In Alkaline Pre-Treated Chitosan, And Alkaline Pre-Treated Chitosan And Alkaline Pre-Treated Collagen Mixed Matrices In Vitro Viability of cells after enzymatic dissociation form culture dishes was about 95–100% as estimated with the vital stain tryphan blue. These cells were inoculated into chitosan and alkaline pre-treated chitosan matrices at a seeding concentration of $1 \times 10^5$ cells/matrix (a diameter 8 mm). 1 week after inoculation on chitosan and alkaline pre-treated chitosan matrices, these matrices were trypsinized, and viable dislodged cells were counted under a light microscopy. The following Table 1 shows viable fibroblast cell numbers in chitosan matrices 1 week after inoculation.

TABLE 1

Fibroblast Cell Numbers In Chitosan Matrices One Week After Inoculation ($1 \times 10^4$ Cells)

|  | Chitosan Matrix | Alkaline Pre-Treated Chitosan Matrix |
|---|---|---|
| control | 6.0 ± 2.0 | 42.7 ± 10.6 |
| + fibronectin (100 ng/ml) | 22.7 ± 3.4 | 93.3 ± 6.2 |
| + bFGF (50 ng/ml) | 68.4 ± 16.1 | 312.9 ± 63.0 |
| + type-Ip collagen (1.5 mg/ml) | — | 332.0 ± 44.0 |

* The above experimental data were obtained by SEM (±) (— shows no detection; n = 4)

Compared to the first seeding concentration, viable cells grown in chitosan matrix decreased about 40%, but increased about 427% in alkaline pre-treated chitosan matrix. In the estimation of viability on fibronectin (100 ng/ml) mixed chitosan and alkaline pre-treated chitosan matrices, viable cells markedly increased approximately 5.5 and 2 times compared to those in chitosan and alkaline pre-treated chitosan matrices, respectively. The number of cells grown in bFGF (50 ng/ml) mixed chitosan and alkaline pre-treated chitosan matrices significantly increased about 17 and 9 times compared to that in both chitosan and alkaline pre-treated chitosan matrices. Also, in type-Ip collagen (1.5 mg/ml) mixed alkaline pre-treated chitosan matrix, it increased about 9 times compared to that in alkaline pre-treated chitosan matrix.

(4) Cytological/Biochemical Analysis OF A Bioartificial Dermis

The bioartificial dermis with human dermal fibroblasts cultured for 1 week was removed from the culture dish and then washed with phosphate buffered saline three times. The dermis was exposed to 0.25% trypsin solution for 10 minutes to isolate fibroblasts from the bioartificial dermis. The dermis was agitated in a petri-dish and then washed with DMEM medium to obtain a suspension. The resulting suspension was added to a plastic test tube containing 10% fetal bovine serum and centrifuged for 5 minutes. 1 ml of DMEM medium was added to cell pellet to obtain a suspension. 100 ml of the resulting suspension was stained with a tryphan blue solution and viable cells were counted under a light microscopy. The results are shown in the following Table 2.

TABLE 2

Viable Human Dermal Fibroblast Numbers In Chitosan Matrices One Week After Attachment Of The Cells Onto The Matrices (1 × $10^4$ Cells)

|  |  | Alkaline Pre-Treated Chitosan Matrix | Alkaline Pre-Treated Chitosan And Alkaline Pre-Treated Collagen Mixed Matrix (1.2 mg/ml of type-Ip collagen) |
|---|---|---|---|
| control |  | 8.5 ± 1.2 | 41.5 ± 1.9 |
| + | 5 ng/ml | 18.0 ± 1.4 | 37.0 ± 2.1 |
| bFGF | 50 ng/ml | 33.5 ± 2.1 | 88.0 ± 2.7 |
|  | 500 ng/ml | 24.0 ± 3.4 | 98.0 ± 3.5 |
| + | 5 ng/ml | 16.0 ± 2.2 | 44.3 ± 1.2 |
| FN | 50 ng/ml | 23.5 ± 0.9 | 58.3 ± 2.7 |
|  | 500 ng/ml | 20.0 ± 1.7 | 58.0 ± 3.2 |

*The above experimental data were obtained by SEM (±) (n = 4)

As shown in the above Table 2, one week after loading the cells onto the matrix, viable cells in the alkaline pre-treated chitosan and alkaline pre-treated type-Ip collagen mixed matrix increased 5 times compared to those in the alkaline pre-treated chitosan matrix. Viable cells in the alkaline pre-treated chitosan matrix comprising 5, 50 and 500 ng/ml of bFGF increased 2, 4 and 3 times compared to those in the alkaline pre-treated chitosan matrix comprising no bFGF, respectively. Viable cells in the alkaline pre-treated chitosan matrix comprising 5, 50 and 500 ng/ml of fibronectin increased 2, 4 and 3 times compared to those in the alkaline pre-treated chitosan matrix comprising no fibronectin, respectively.

Additionally, viable cells in the alkaline pre-treated chitosan and alkaline pre-treated collagen mixed matrix comprising 5, 50 and 500 ng/ml of bFGF increased 4.5, 10 and 11.5 times compared to those in the alkaline pre-treated chitosan and alkaline pre-treated collagen mixed matrix comprising no bFGF, respectively. Viable cells in the alkaline pre-treated chitosan and alkaline pre-treated collagen mixed matrix comprising 5, 50 and 500 ng/ml of fibronectin increased 5, 7 and 7 times compared to those in the alkaline pre-treated chitosan and alkaline pre-treated collagen mixed matrix comprising no fibronectin, respectively.

Figure 3:
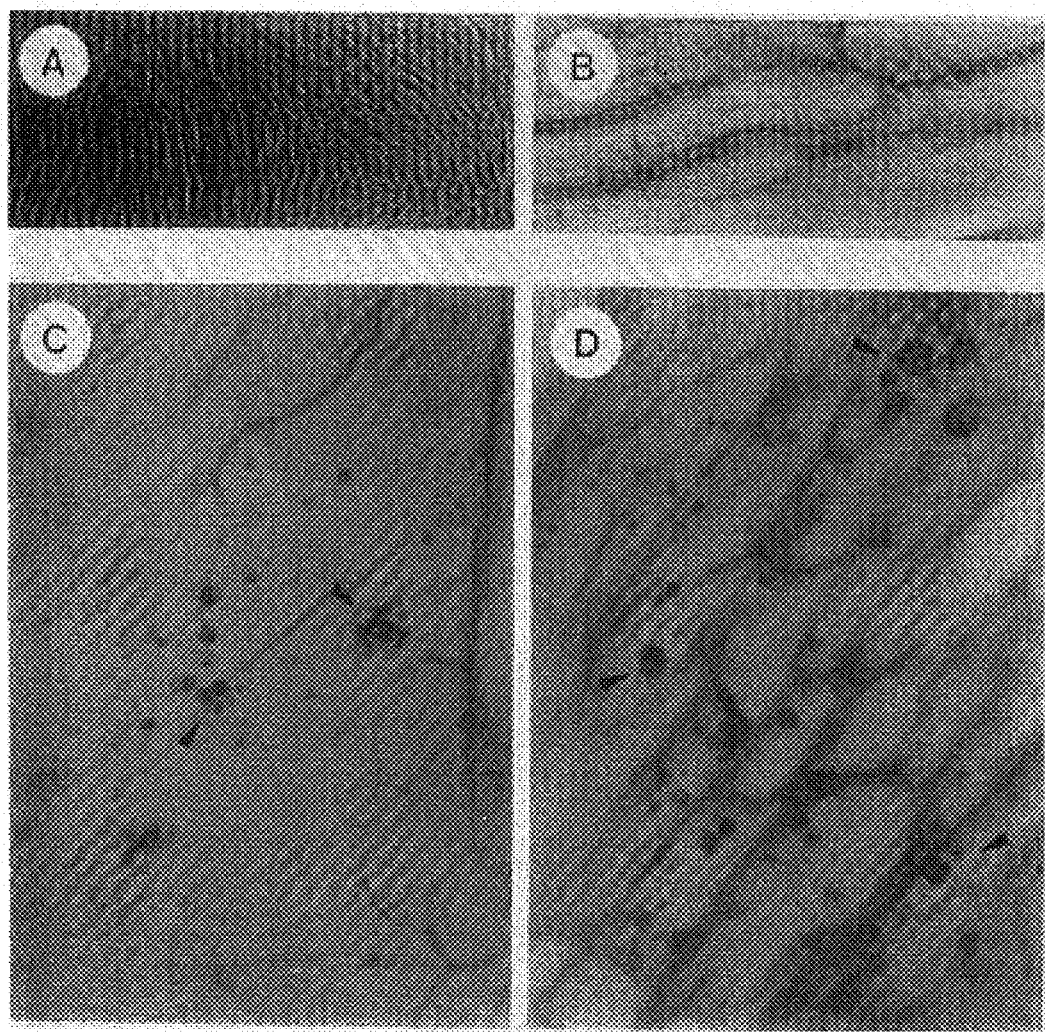
FIG. 3 shows alkaline pre-treated free amine-containing chitosan matrix comprising human fibroblasts containing bFGF (50 ng/ml) or no bFGF, viewed using light microscopy (magnification×200)

FIG. 3 shows cultured human fibroblasts (A), alkaline pre-treated chitosan matrix (B), alkaline pre-treated chitosan matrix with cultured human fibroblasts containing no bFGF (C) and alkaline pre-treated chitosan matrix with cultured human fibroblasts containing bFGF (D). Arrows indicate healthy fibroblasts in the chitosan-matrix fibers.

Figure 4:
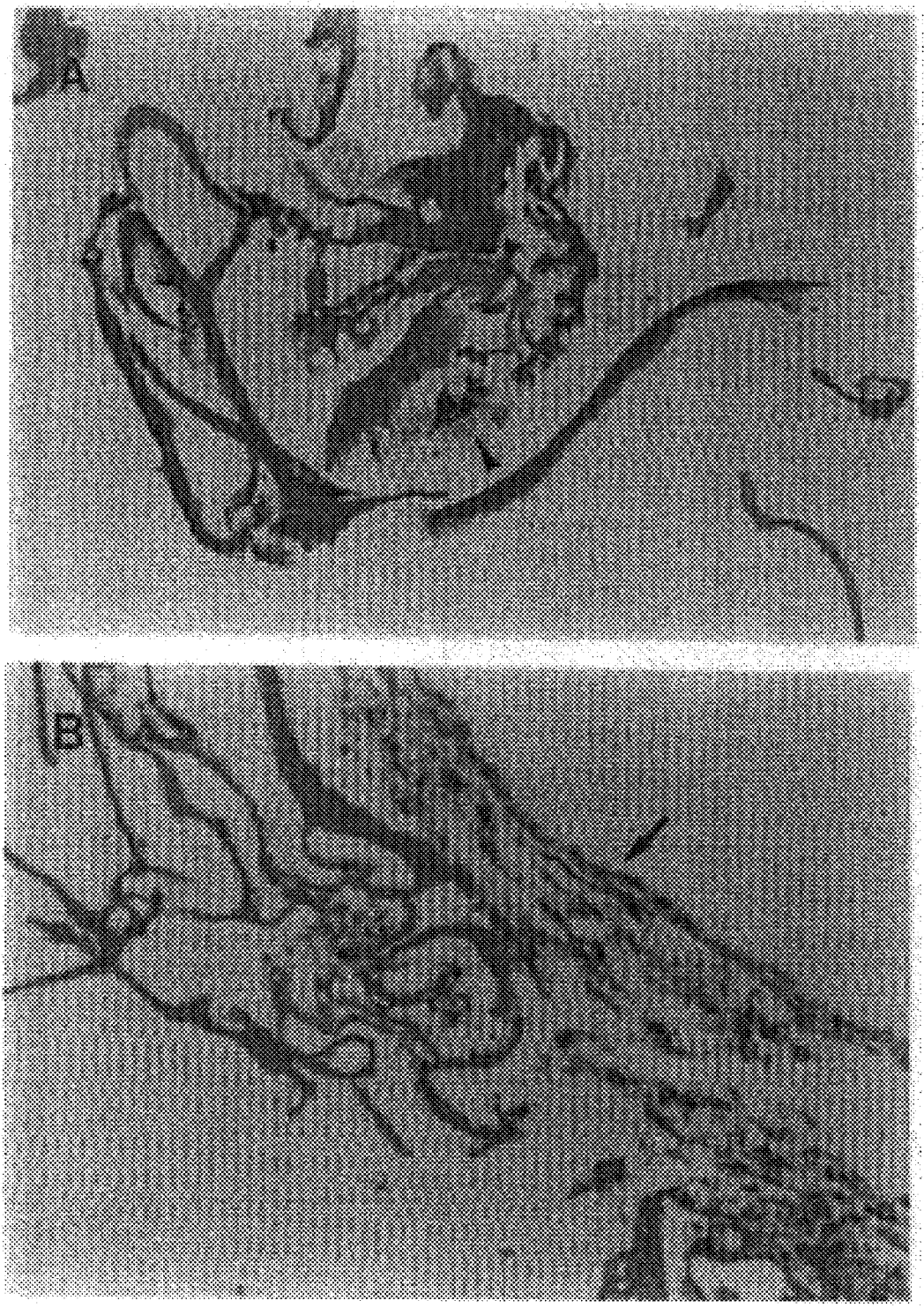
FIG. 4 shows histology of the cross-sections on alkaline pre-treated free amine-containing chitosan matrix (A) and alkaline pre-treated free amine-containing chitosan and alkaline pre-treated collagen mixed matrix (B) with cultured human fibroblasts for 4 weeks in vitro (magnification×200)

Sections of the alkaline pre-treated chitosan or the alkaline pre-treated chitosan and alkaline pre-treated collagen mixed matrix were fixed with 10% formalin/phosphate buffered saline and dehydrated in ethanol. Then, they were washed with xylene and embedded in paraffin overnight. The embedded tissues were sectioned at a thickness of 4 $\mu$m using a rotary microtome and the sectioned tissues were stained with hematoxylin-eosin (H&E). The alkaline pre-treated chitosan matrix, particularly, the first few weeks fibroblast growth on the chitosan matrix, tore easily during sectioning. However, the matrix with the fibroblasts cultured for 4 weeks had the improved structural integrity and was sectioned more easily with less disruption (FIG. 4: magnification×200).

In FIG. 4(A) (alkaline pre-treated chitosan matrix), the matrix had little structural integrity and brittle. Human fibroblasts were disrupted during sectioning and rarely shown. Arrows indicate chitosan fibers.

In FIG. 4(B) (alkaline pre-treated chitosan and alkaline pre-treated collagen mixed matrix), the matrix had much more integrity than that in (A). This probably resulted from matrix protein secreted from the cells and collagen fibers. The matrix maintained the structural integrity during sectioning. Arrowheads indicate human fibroblasts and matrix fibers.

Example 3

Grafting Experiment for in Vivo Application of a Bioartificial Dermis in Balb/c Mouse (1) Grafting Of An Artificial Dermis Balb/c mice were bred in a sterile room. Surgery and grafting were performed in laminar-flow hoods and anesthesia was performed by intraperitoneal injection of 3 ml/kg of equithesin. A depilatory was applied onto the dorsal sides of the mice and the hair coat was clipped off and then, the depilated area was disinfected with povidone-iodine and 70% isopropyl alcohol. A full-thickness disk of skin was excised using an autopsy puncture. This excision resulted in approximately 5% total body surface area of skin defect in the experimental animals. Acellular and cellular artificial dermises of the same size as the excision were grafted onto the wound bed and covered with a sterile gauze dressing. To prevent infection, the mice were provided with water supplemented with ampicillin and streptomycin.

The animals were examined for integrity of grafts and healing process everyday and sacrificed after 10 days and 4 weeks. The animals were photographed and tissue was obtained for the following histological analysis.

Figure 5:
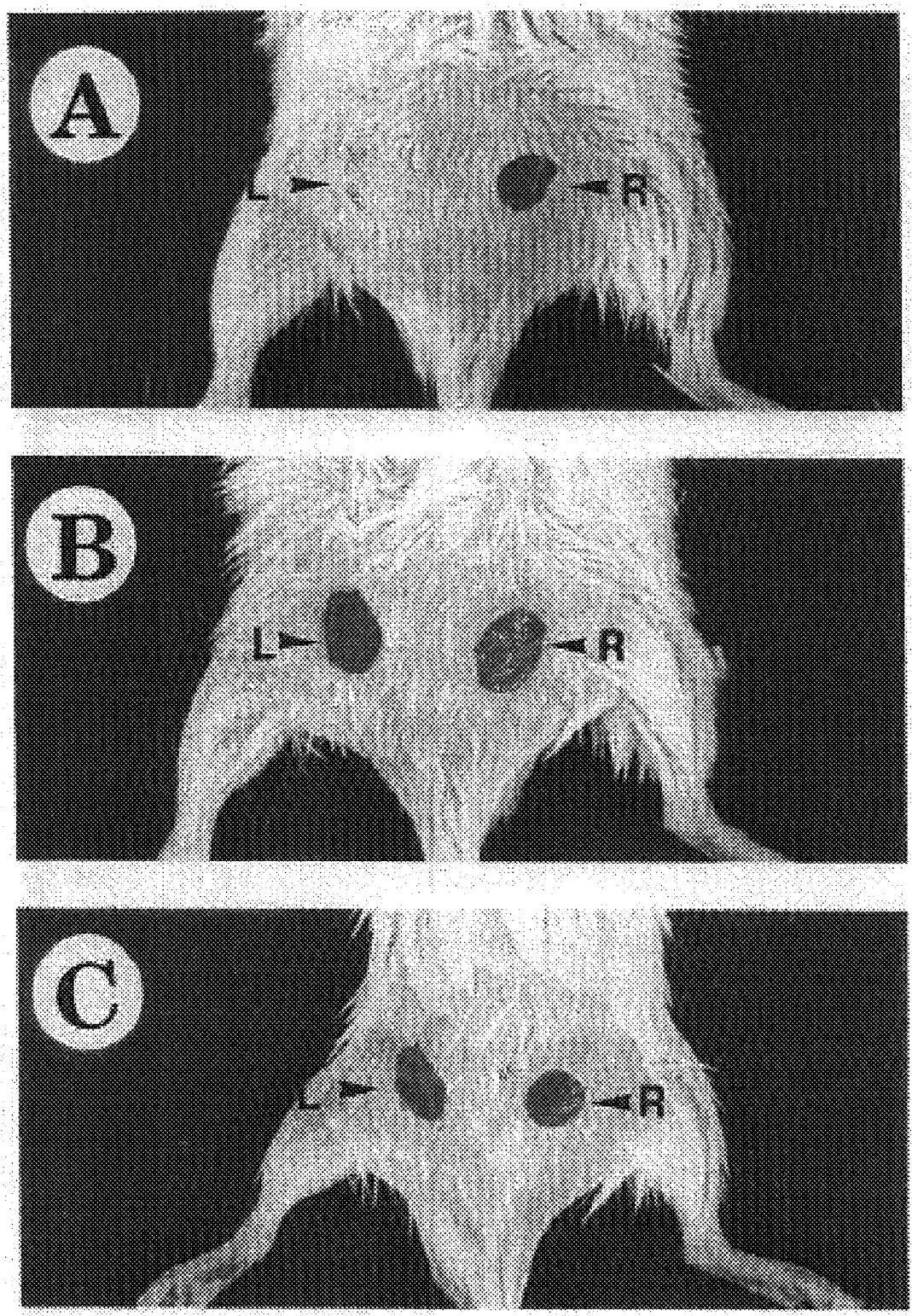
FIG. 5 shows chitosan matrix grafts on the full-thickness excision in the Balb/c mouse.

FIG. 5 shows chitosan-matrix grafts on the full-thickness excision in Balb/c mouse. In FIG. 5(A), the right (R) indicates no graft (control) and the left (L) indicates the alkaline pre-treated chitosan matrix. In FIG. 5(B), R indicates alkaline pre-treated type-Ip collagen matrix and L indicates alkaline pre-treated chitosan matrix. In FIG. 5(C), R indicates alkaline pre-treated type-Ip collagen+fibronectin matrix and L indicates alkaline pre-treated chitosan+type-Ip collagen+fibronectin matrix, respectively. These matrices tightly adhered to wound bed and have no fluid collections.

Figure 6:
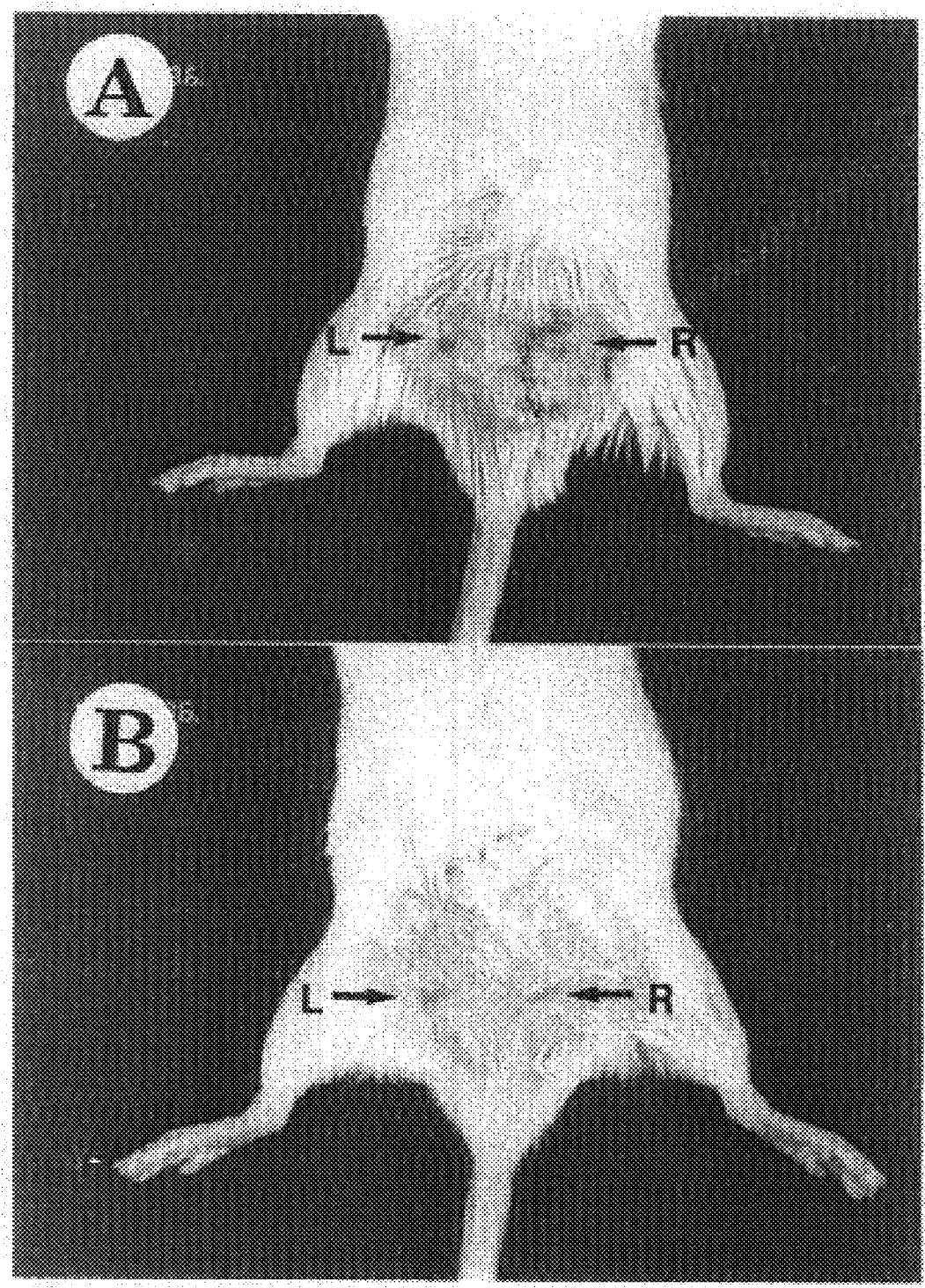
FIG. 6 shows graft sites in Balb/c mouse 4 weeks after grafting.

FIG. 6 shows graft site in Balb/c mouse 4 weeks after grafting. In (A), R indicates control and L indicates alkaline pre-treated chitosan matrix. In (B), R indicates alkaline pre-treated type-Ip collagen matrix, L indicates alkaline pre-treated chitosan+type-Ip collagen matrix, respectively. It was shown that scar remained in control but the wounds were well healed in the other grafts.

(2) Preparation Of Tissue Specimen And Histological Analysis

Tissue specimen from the animal wound was obtained by excision of the entire graft with a surrounding rim of normal mouse skin and underlying panniculus carnosus. The sample was fixed with 10% formalin/phosphate buffered saline and embedded in paraffin. Then, it was sectioned according to the same procedure as above and the result was obtained by staining with hematoxylin-eosin.

Figure 7:
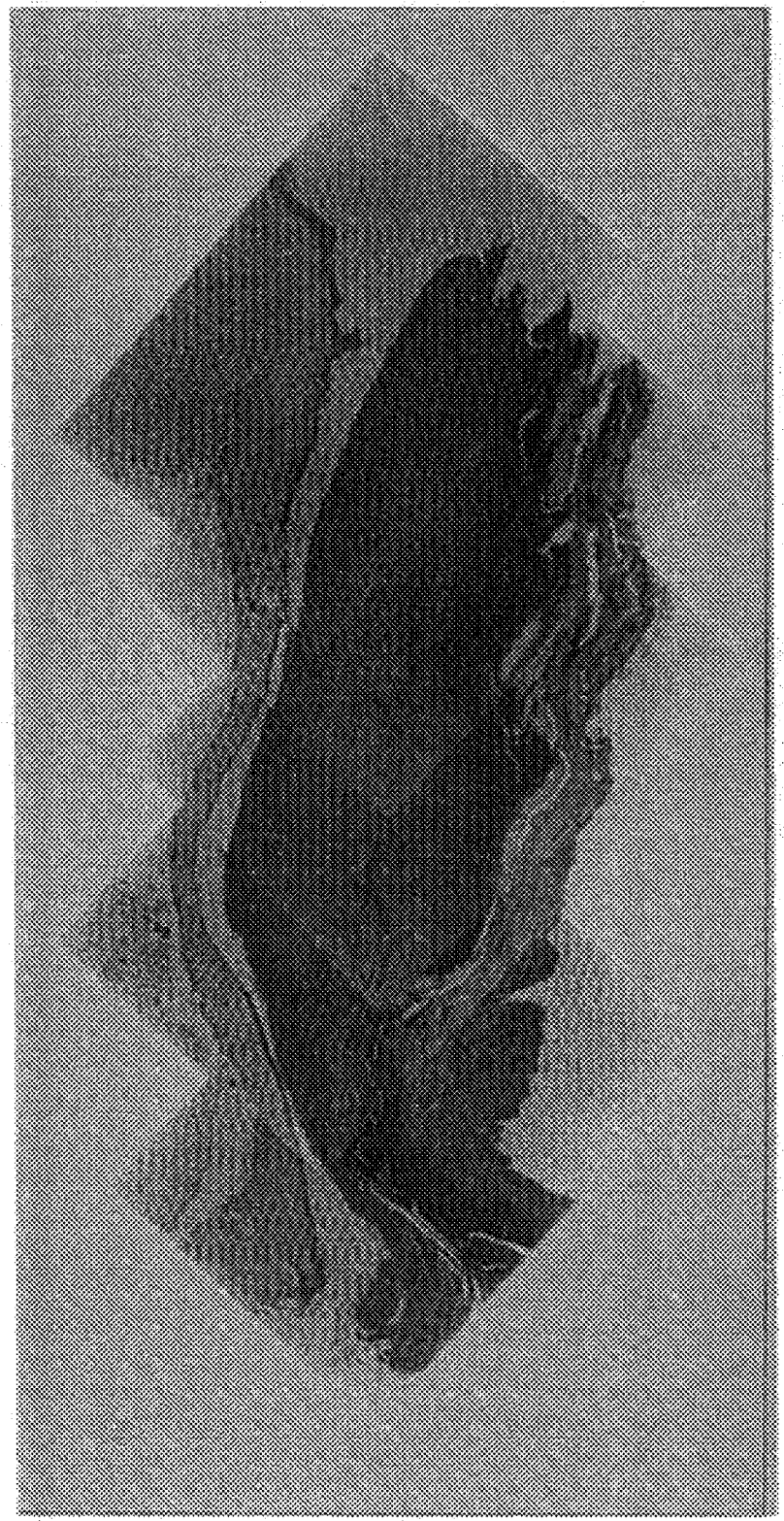
FIG. 7 shows gross histology of control biopsied from the dorsolateral region of Balb/c mouse 10 day after grafting.

FIG. 7 shows gross histology of control biopsied from the dorsolateral region of Balb/c mouse 10 day after grafting (hematoxylin-eosin staining, magnification 100×). This area was not fully epithelialized, and did not reconstruct the neodermis and exhibited severe inflammation. This poor healing may caused by the lack of a dermis.

Figure 8:
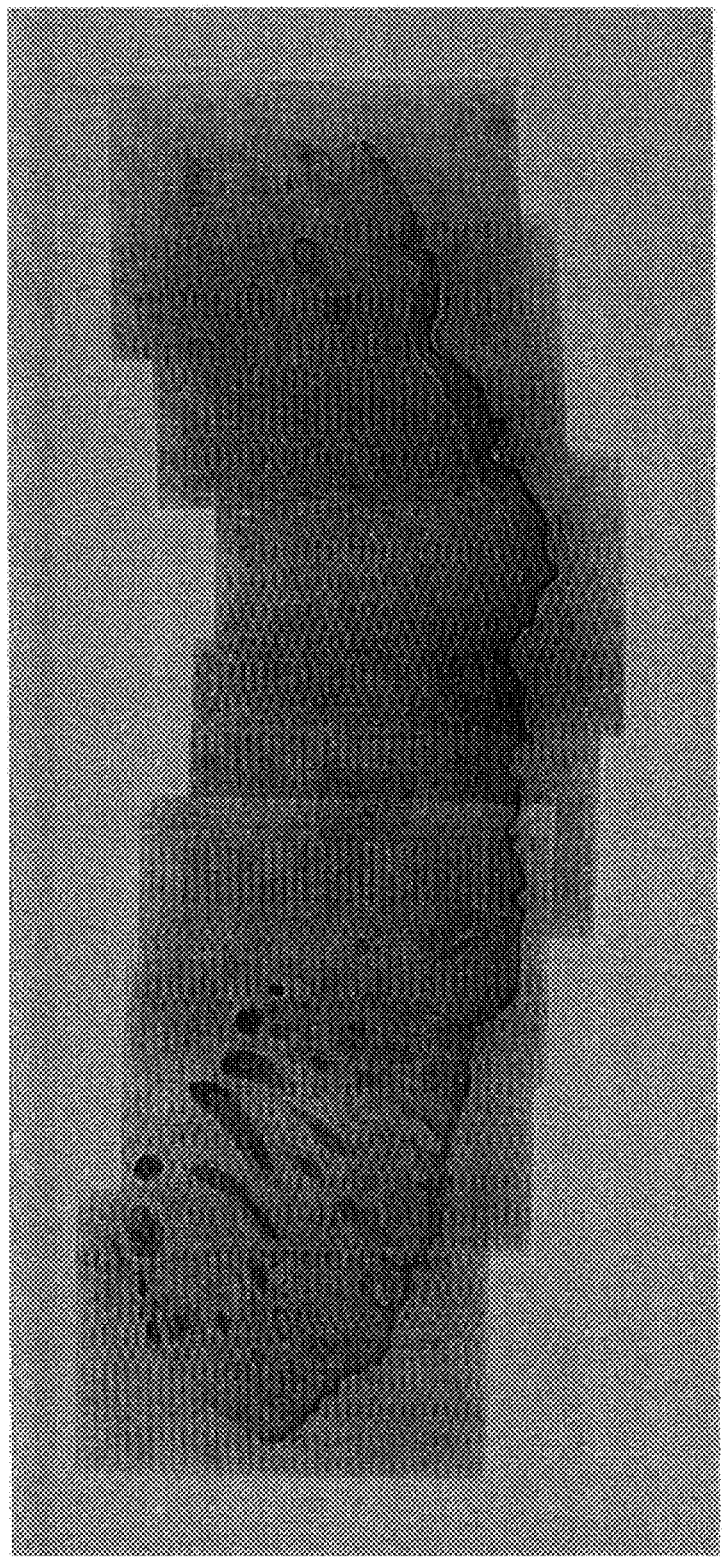
FIG. 8 shows gross histology of graft site biopsied from the dorsolateral region of Balb/c mouse grafted with alkaline pre-treated chitosan matrix 10 days after grafting.

FIG. 8 shows gross histology of graft site biopsied from the dorsolateral region of Balb/c mouse grafted with alkaline pre-treated chitosan matrix 10 days after grafting. Normal skin tissue was found on both sides (determined by many follicular cells which were stained red) and newly regenerated epidermis and dermis were found in the middle. Multi-layered epidermis was formed and dermal cells were migrated into the wound site to reconstruct the neodermis and further, no inflammation was observed.

Figure 9:
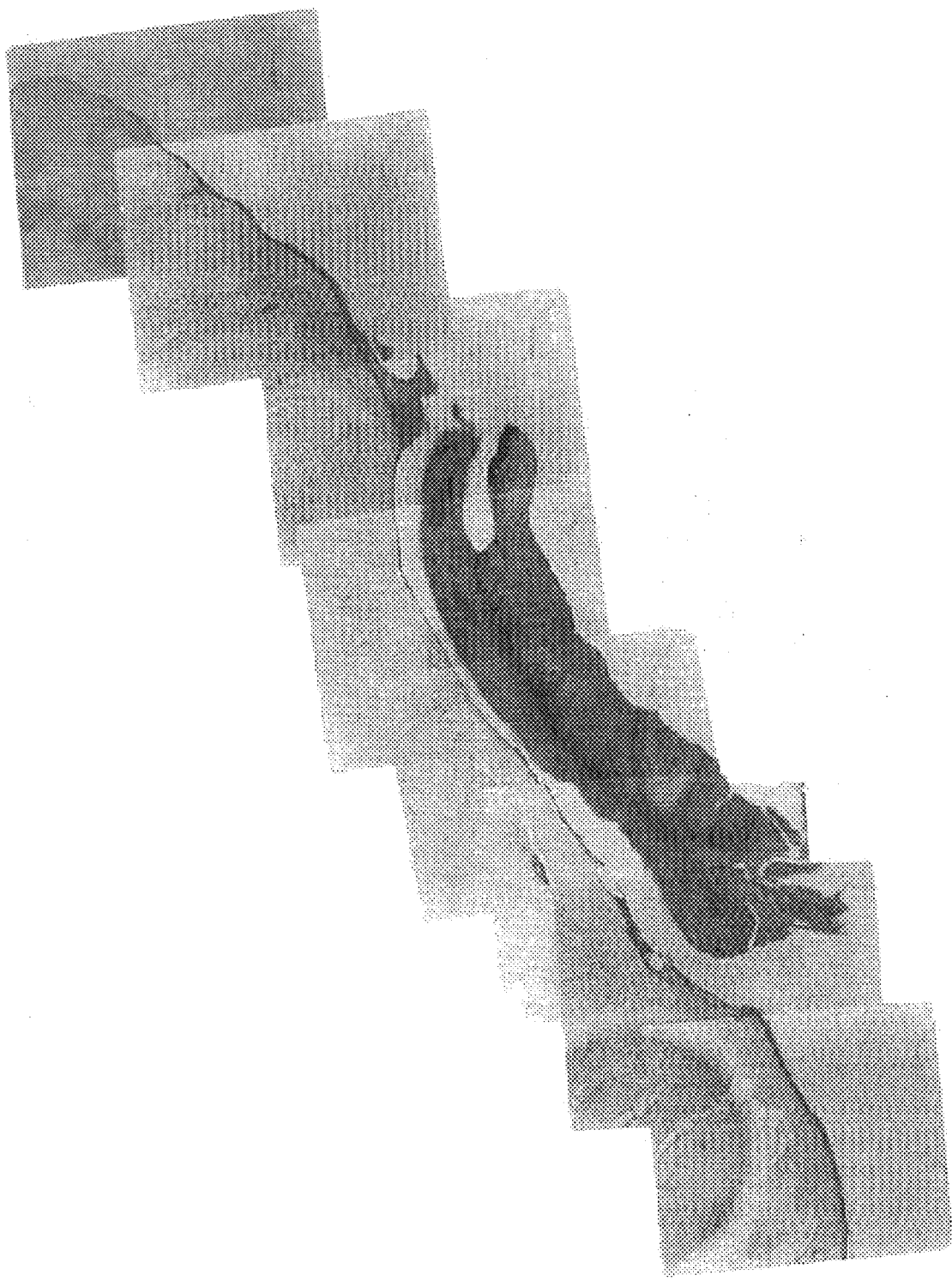
FIG. 9 shows gross histology of a graft site biopsied from the dorsolateral region of Balb/c mouse grafted with alkaline pre-treated free amine-containing chitosan+bFGF (50 ng/ml) matrix 10 days after grafting.

FIG. 9 shows gross histology of graft site biopsied from the dorsolateral region of Bal/c mouse grafted with alkaline pre-treated chitosan matrix containing 50 ng/ml of bFGF 10 days after the grafting. In the similar pattern to alkaline pre-treated chitosan matrix, normal skin tissue was found on both sides and newly regenerated epidermis and dermis were found in the middle. In comparison with alkaline pre-treated chitosan matrix, a little inflammation was accompanied but on the whole, satisfactory healing effect was obtained.

Figure 10:
FIG. 10 shows gross histology of a graft site biopsied from the dorsolateral region of Balb/c mouse grafted with alkaline pre-treated free amine-containing chitosan+type-Ip collagen matrix 10 days after grafting.

FIG. 10 shows gross histology of graft site biopsied from the dorsolateral region of Balb/c mouse grafted with alkaline pre-treated chitosan/type-Ip collagen mixed matrix 10 days after the grafting. Intact multi-layered epidermis and the reconstructed neodermis were found and further, follicular cells were also found.

Example 4

Cytotoxicity Test of a Chitosan Derivates in Vitro $1 \times 10^4$ of human dermal fibroblast cells in 96 well plate were cultured in DMEM medium supplemented with 100 µl of 10% serum. Then, the cultured cells were treated with 5, 50, and 500 ng/ml of chitosan oligomer, CM-chitin and 3,6-S-chitin, respectively. 48 hours after treatment, MTT (3-[4,5-dimethylthiazol-2-yl]-2,5-diphenyltetrazolium bromide; Thiazolyl blue, Sigma Product No. M5655) was added thereto and then, the mixture was allowed to stand for 4 hours. After removal of the culture medium, the resultant mixture was washed with phosphate buffered saline 2–3 times and 100 µl of DMSO (dimethylsulfoxide) was added thereto. After chromogenesis, an absorbance was measured at 545 nm on each well using ELISA reader. The results are shown in Table 3.

TABLE 3

Viability Assay Result Of Human Dermal Fibroblasts Treated With Chitosan Derivates

|  | 5 ng/ml | 50 ng/ml | 500 ng/ml |
| --- | --- | --- | --- |
| chitosan oligomer | 0.629 | 0.618 | 0.733 |
| CM-chitin | 0.603 | 0.630 | 0.603 |
| 3,6-S-chitin | 0.608 | 0.727 | 0.595 |

As shown above, viability of fibroblast cells treated with the chitosan derivates was in the range of 87.9 to 108.2% of that of control. Therefore, the chitosan derivates were confirmed to have little cytotoxicity in vitro. Since the alkaline pre-treated chitosan and alkaline pre-treated collagen mixed matrices of the present invention are degraded to such chitosan derivates, it is contemplated that they are substantially non-toxic in vivo.

Accordingly, the dermal scaffold according to the present invention has excellent wound healing effect by constituting microenvironments suitable for migration and proliferation of fibroblasts and vascular cells surrounding the wound, which is extremely useful as wound healing dressings, and the bioartificial dermis comprising the dermal scaffold and human fibroblasts is particularly useful for healing broad wound sites such as burns wherein migration of the surrounding cells is difficult.

Example 5

Comparison in Structural Stability (Spongy Scaffold vs. Mesh Scaffold)

1) Preparation Of Comparative Samples
a) Preparation Of Spongy Matrix

The spongy matrices of alkaline pre-treated chitosan scaffolds were prepared according to the procedure of Example 1(2).

B) Fabrication Of Non-Woven Mesh

A chitosan filament was wet spun by generally following the methods described in G. C. East, J. E. Mcintyre and Y. Qin. Proc. 4$^{th}$ Internat. Conf. On Chitin and Chitosan, eds. S. Tokura and P. Stanford, 1988, pp. 757–763). A spin dope was prepared by dissolving 5% w/v chitosan in 5% v/v aqueous acetic acid. After removal of impurities and insolubles by filtration with glass fiber (G2), refined chitosan dope was spun through nozzle (diameter: 0.1 mm) into a mixed alkaline solution (saturated KOH in 50% ethanolic solution) at room temperature. Resulted filaments were continuously stretched by winding up onto bobbin (rate: 30 m/min), then passed through ethanol bath and successively washed with hot and cold water. Regenerated chitosan fibers were dried in hot air. 5 mm of the chitosan fibers dispersed in chitosan solution (2 wt %). After 1 hour, excess chitosan solution was removed. Non-woven mesh scaffolds were obtained by vacuum drying at 150° C. for 24 hours.

2) Results

A) Structural Stability: Pretest For Dynamic Cell Loading And Culture

Figure 11:
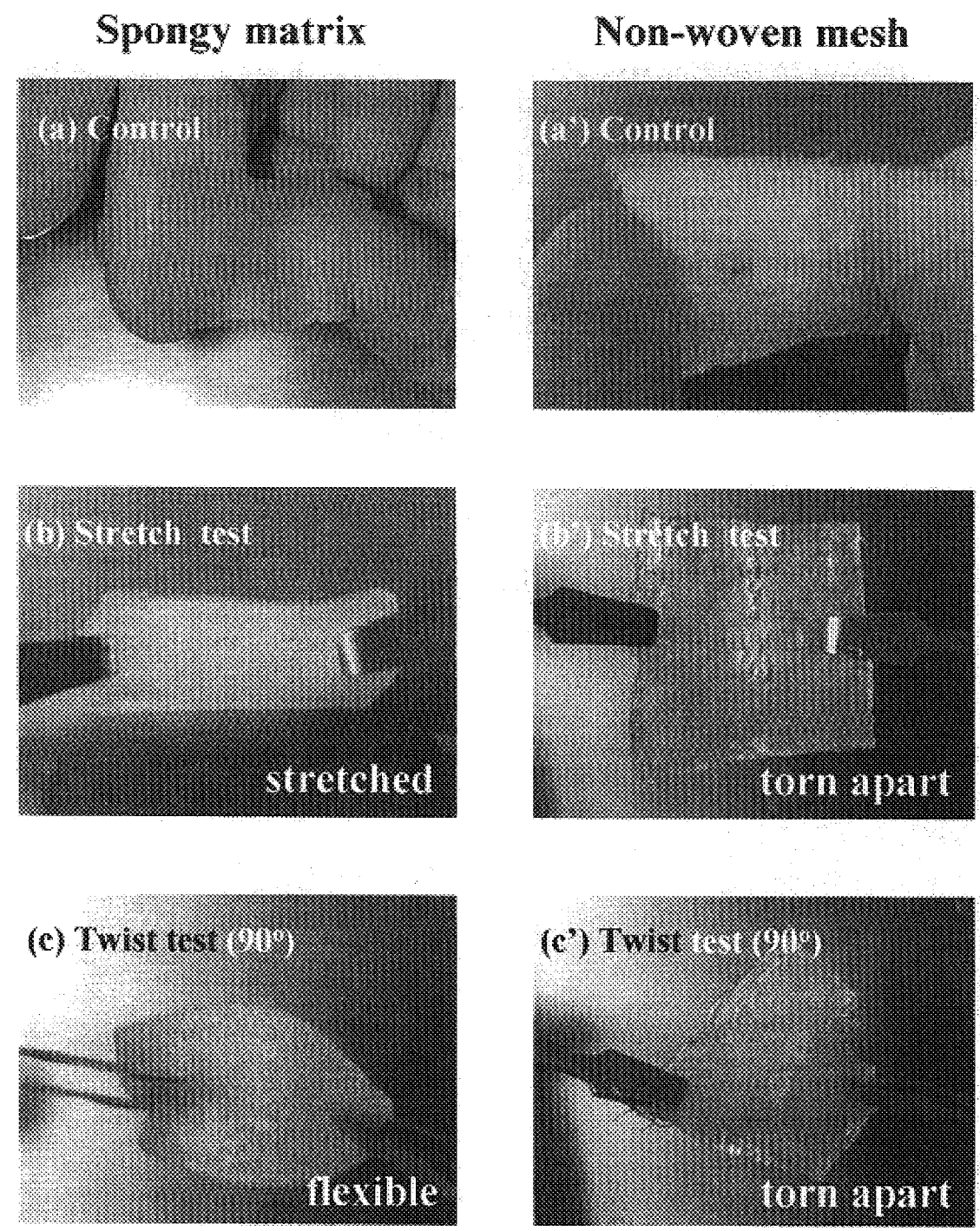
FIG. 11 shows the results of stretch, twist and structural stability tests of the spongy matrix and non-woven mesh of chitosan in wet state for dynamic cell loading and skin grafting.

Dermal scaffolds of the present invention and the above non-woven mesh were slowly agitated (about 60 rpm) in deionized water using a magnetic stirrer for desired time. The results are shown in Table 4 and FIG. 11.

TABLE 4

Structural Stability Of Spongy Matrix And Non-Woven Mesh

|  | Spongy matrix | Non-woven mesh |
| --- | --- | --- |
| Maintenance of original shape |  |  |
| 2 h spinning | Original shape | Fibers detached from the mesh |
| 16 h spinning | Original shape | Complete demolition of the mesh |
| Tensility test |  |  |
| Stretch | Stretchable | Torn apart |
| Twist | Twistable | Torn apart | b) Morphology

The mesh type dermal scaffold was composed of non-woven chitosan fibers. Since more chitosan per unit cm$^3$ was necessary for the production of fibers, the mesh composed of fibers was more brittle and stiff. Due to the higher chitosan density in the mesh than the spongy matrix, the mesh appeared to yellowish, even though the same material was used. When it got wet, the spongy matrix formed tangible and flexible hydrated spongy dermal scaffold, which was very easy to handle for further process such as graft or cell loading.

Example 6

SEM (Scanning Electron Microscopy) Morphology

The scaffolds of the present invention and the non-woven mesh type scaffolds were fixed for examination under SEM. The scaffolds were washed with phosphate-buffered saline and then, fixed in PBS buffer containing 1% glutaraldehyde at room temperature for 1 hour. Then, the scaffolds were incubated at 4° C. for 24 hours. After washing with PBS buffer, the scaffolds were dehydrated through a graded series of 50, 60, 70, 80, 90 and 100% ethanol for 10 minutes each. The samples were critically point dried and coated with an ultra-thin gold layer (100 Å).

Freeze-drying was used for the preparation of the chitosan scaffold, which makes very homogeneous porous structure. By adjusting freezing temperature, pore size can be easily manipulated, which makes more advantageous over the mesh type in its processibility. Furthermore, the method for preparing the spongy matrix was very simple and reproducible.

SEM morphologies of the sponge types of chitosan scaffolds prepared at different freezing temperature are shown in FIG. 12($a$–$d$) and those of the mesh type of non-woven chitosan scaffolds are shown in FIG. 12($e$ and $f$). The chitosan scaffolds showed a well-interconnected microporous structure (pore size ranging from 150 to 250 $\mu$m). The morphologies of HDF-loaded chitosan scaffolds are shown in FIG. 12($g$ and $h$). Because of this porosity of chitosan scaffold, chitosan scaffolds coated with type I collagen and either bFGF or fibronectin could provide more favorable environment for the growth and differentiation of human dermal fibroblasts. That is, HDFs were well grown and the spongy matrix was enveloped with extracellular matrix secreted therefrom.

Figure 13:
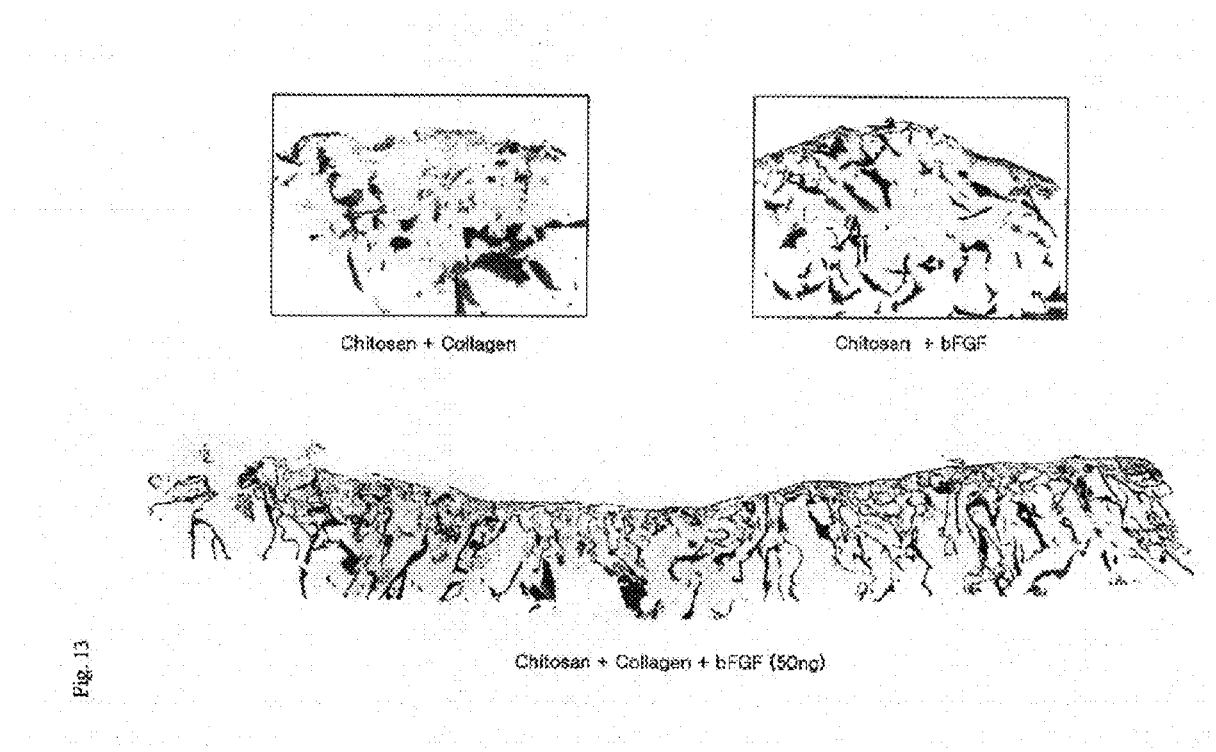
FIG. 13 shows the results of H&E staining of dermal scaffold at 14 days after seeding human dermal fibroblasts in vitro (magnification×200)

Then, in order to examine the state of the cells within the spongy matrix, the cross section was observed with H&E staining. The results are shown in FIG. 13. As shown in FIG. 13, the framework of the spongy matrix was well maintained. It was also confirmed that the matrix effectively functioned as a scaffold to help the ingrowth of the seeded cells and thus, the cells were well seeded into the inside of the matrix.

Example 7

Implantation Experiment For In Vivo Application Of Dermal Scaffold Comprising Alkaline Pre-treated Chitosan Matrix 1) Implantation
a) In Vivo Application Fisher 344 rats (~170 g, 7 week old) were bred in a sterile room. Surgery and implantation were performed in laminar-flow hoods and anesthesia was carried out by intraperitoneal injection of a mixture of ketamine (80 mg/kg) and xylazine (5 mg/kg). Hairs were removed by clipper and sterilized with 70% alcohol. Incision was made on the inter-scapular region with a blade and blunt dissection with scissors was carried out. Saline-soaked 8 mm implant was inserted. Wound was closed by interrupt suture. The animals were examined for integrity of grafts and healing process every day and sacrificed after 7 days and 15 days. The animals were photographed and tissue was obtained for the following histological analysis.

B) Preparation Of Tissue Specimen And Histological Analysis

The rat was anesthetized and the implant was removed. The tissue was fixed with a neutralized formalin/phosphate saline and embedded in paraffin and then, 4 $\mu$m section was prepared according to the general pathological protocol. Hematoxylin and Eosin staining, Masson's Trichome staining and immunohistochemical staining for Smooth Muscle Action were followed by the general pathological protocol.

2) Results

Figure 14:
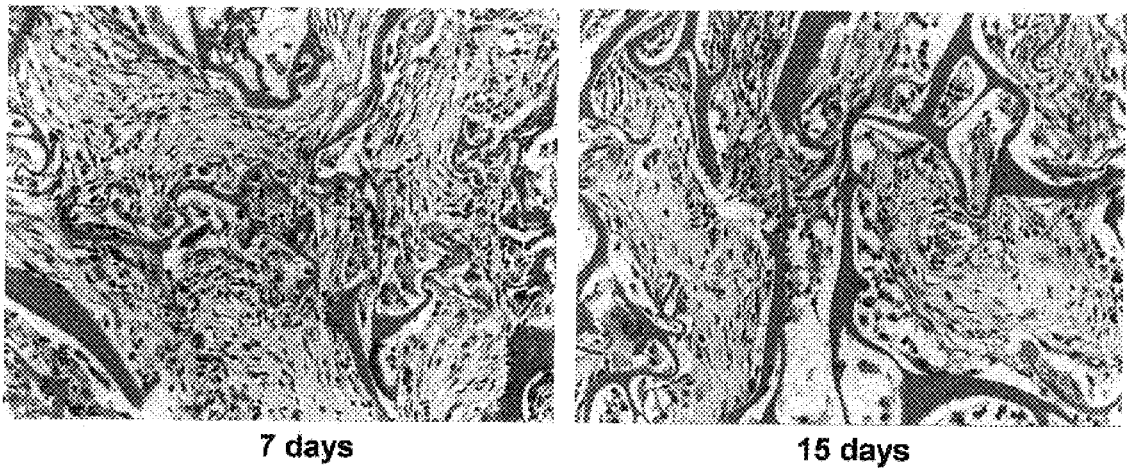
FIG. 14 shows the results of H&E staining of the chitosan sponge implant (the chitosan sponge: thin red fiber; collagen bundles: pink; cells: purple; and RBC: red)
Figure 15:
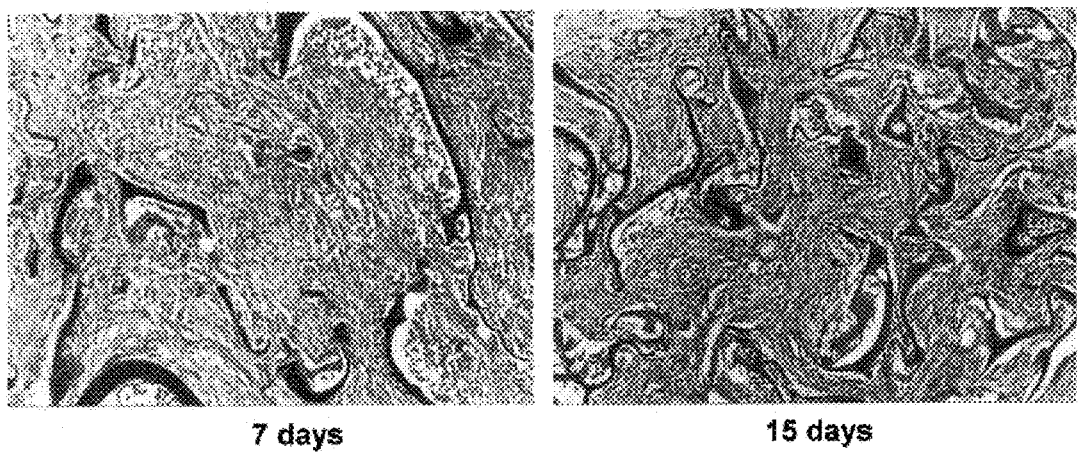
FIG. 15 shows the results of Masson's Trichome staining of the chitosan sponge implant (the chitosan sponge: thin red fiber; collagen bundles: green; cells: purple; and RBC: red); and, FIG. 16 shows the results of immunohistochemical staining for Smooth Muscle Actin (α-SMA) of the chitosan sponge implant.

The results are shown in FIGS. 14 to 16. As shown in the Figures, the framework of the spongy matrix was maintained at 15 days after implantation and it effectively functioned as a scaffold helping the ingrowth of the surrounding cells. After 7 days, almost inflammatory cells disappeared and tissue was vigorously regenerated. Formation of microvessels infiltrated with the surrounding cells was observed in the implanted matrix. The above results were due to an excellent biocompatibility of the chitosan scaffold. Below, the results will be described in more detail.

a) After 7 Days

Polymorphonuclear (PMN) cells that had been present in the connective tissue surrounding the chitosan sponge were decreased and a number of fibroblasts at the margin of sponge were infiltrated into the center of the sponge. Fibroblasts and PMN cells were found in a high density along with the frame (fibroplasia), and macrophages and polynuclear cells (giant cells) were found in the groove. Further, in the sponge, venuoles composed of 1 to 2 vascular endothelial cells were found, and red blood cells were observed in the further developed microvessels (FIG. 14). For more detailed observation, α-Smooth Muscle Actin specifically stained at the margin of the vessel was observed and as a result, formation of a number of vessels, which were stained dark brown at the margin (FIG. 16; denoted as circles) was found.

Such the infiltration of fibroblasts and PMN cells into the implant is similar to the granulation formation during wound healing stages in full-thickness wound. The presence of a number of vascular endothelial cells among the infiltrated cells into the sponge indicates that the porous chitosan sponge maintains its shape during the wound-healing period thereby to promote the infiltration of fibroblasts and angiogenesis.

b) After 15 Days

Only the decreased number of fibroblasts and macrophages were found in the connective tissue surrounding the sponge. Fibroblasts infiltrated into the sponge were decreased, but collagen, one of extracellular matrices secreted by the fibroblasts, was increased. As shown in FIG. 15, much more matured dark green collagen bundles were observed. Collagen was predominantly formed in the part where fibroblasts are present at a high density, and the number of microvessels with endothelial cells was increased. The polynuclear cells were retained in the groove and the shape of fibroblasts was changed thin and long. Fibroblasts were locally present at a high density in the sponge.

A general would healing process consists of 1) inflammatory stage, 2) granulation stage and 3) matrix formation (remodeling). It can be seen from the above results that after 15 days, granulation stage had been completed and matrix formation (remodeling) was begun. It is also contemplated that most healing stages like formation of microvessels has been completed within 7 days. The chitosan sponge implant showed similar would-healing process to that usual in a wound. Therefore, the sponge is confirmed to be an extremely useful material for wound healing.

Variations, modifications, and other implementations of what is described herein will occur to those of ordinary skill in the art without departing from the spirit and scope of the invention and claims.

All references, patents, and patent applications described herein, are incorporated herein in their entireties.

What is claimed is:

1. A dermal scaffold comprising alkaline pre-treated free amine-containing chitosan and alkaline pre-treated collagen mixed matrix of a porous spongy structure, which is insoluble in an aqueous medium or a body fluid thereby to provide a structural integrity for migration and proliferation of wound healing cells surrounding wound site.

2. The dermal scaffold of claim 1, wherein said alkaline pre-treated free amine-containing chitosan and alkaline pre-treated mixed matrix is prepared by the method comprising the steps of:
   a) pre-treating an acidic chitosan solution with an alkaline solution to obtain free amine-containing chitosan solution;
   b) pre-treating an acidic collagen solution with an alkaline solution;
   c) mixing the alkaline pre-treated free amine-containing chitosan solution prepared in step a) with the alkaline pre-treated collagen solution prepared in step b); and,
   d) lyophilizing the mixed solution prepared in step c).

3. The dermal scaffold of claim 1, further comprising one or more selected from the group consisting of fibronectin, basic fibroblast growth factor, epidermal growth factor and transforming growth factor-$\beta$.

4. A bioartificial dermis wherein human fibroblasts are attached into the dermal scaffold as defined in any one of claims 1 to 3.

5. A dermal scaffold comprising alkaline pre-treated free amine-containing chitosan and alkaline pre-treated collagen mixed matrix containing chitosan fabrics of a porous spongy structure, which is insoluble in an aqueous medium or a body fluid thereby to provide a structural integrity for migration and proliferation of wound healing cells surrounding wound site.

6. The dermal scaffold of claim 5, wherein said alkaline pre-treated free amine-containing chitosan and alkaline pre-treated collagen mixed matrix containing chitosan fabrics is prepared by the method comprising the steps of:
   a) weaving chitosan fibers into fabrics;
   b) pre-treating an acidic chitosan solution with an alkaline solution to obtain free amine-containing chitosan solution;
   c) applying the alkaline pre-treated free amine-containing chitosan solution prepared in step b) onto the chitosan fabrics prepared in step a);
   d) pre-treating a collagen solution with an alkaline solution; and,
   e) coating the alkaline pre-treated free amine-containing chitosan matrix containing chitosan fabrics prepared in step c) with the alkaline pre-treated collagen solution prepared in step d).

7. The dermal scaffold of claim 5, further comprising one or more selected from the group consisting of fibronectin, basic fibroblast growth factor, epidermal growth factor and transforming growth factor-$\beta$.

8. A bioartificial dermis wherein human fibroblasts are attached into the dermal scaffold as defined in any one of claims 5 to 7.

* * * * *